United States Patent
Oonuma

(12) 
(10) Patent No.: US 6,800,787 B2
(45) Date of Patent: Oct. 5, 2004

(54) CATALYST FOR ACIDOLYSIS OF AROMATIC HYDROPEROXY COMPOUND AND PROCESS FOR PRODUCING AROMATIC HYDROXY COMPOUND USING THE SAME

(75) Inventor: Mitsuru Oonuma, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/673,176

(22) Filed: Sep. 30, 2003

(65) Prior Publication Data

US 2004/0073071 A1 Apr. 15, 2004

(30) Foreign Application Priority Data

Oct. 11, 2002 (JP) ........................................ 2002-298484

(51) Int. Cl.[7] .............................................. C07C 37/08
(52) U.S. Cl. ........................ 568/768; 502/172; 502/216; 568/798
(58) Field of Search ................................. 568/768, 798; 502/172, 216

(56) References Cited

U.S. PATENT DOCUMENTS

| 3,923,908 A | * | 12/1975 | Suda et al. .................. 568/768 |
| 3,928,469 A | * | 12/1975 | Suda et al. .................. 568/768 |
| 4,568,768 A | * | 2/1986 | Nakamura et al. ........... 568/311 |
| 6,350,921 B1 | * | 2/2002 | Durairaj et al. ............. 568/771 |
| 6,433,232 B2 | * | 8/2002 | Noritake ...................... 568/768 |

FOREIGN PATENT DOCUMENTS

JP 9-143111 A 6/1997

* cited by examiner

Primary Examiner—Michael L. Shippen
(74) Attorney, Agent, or Firm—Sughrue Mion, PLLC

(57) ABSTRACT

A catalyst for acidolysis of an aromatic hydroperoxy compound, containing little scale, prepared by gasifying liquid sulfuric anhydride and dissolving gasified sulfuric anhydride in a ketone solvent, and a process for producing a hydroxy aromatic compound using the catalyst.

12 Claims, No Drawings

CATALYST FOR ACIDOLYSIS OF AROMATIC HYDROPEROXY COMPOUND AND PROCESS FOR PRODUCING AROMATIC HYDROXY COMPOUND USING THE SAME

BACKGROUND OF THE INVENTION

1. Technical Field

The present invention relates to a catalyst for acidolysis of an aromatic hydroperoxy compound, containing little scale, and a process for producing an aromatic hydroxy compound using the catalyst.

2. Description of Related Art

Aromatic hydroxy compounds, for example, a dihydroxybenzene is produced by acidolysis of a di(hydroperoxyalkyl)benzene, for example, di(2-hydroperoxy-2-propyl)benzene. In the acidolysis of di(2-hydroperoxy-2-propyl)benzene, sulfuric anhydride is used as a catalyst for acidolysis. Sulfuric anhydride has a boiling point of 44.8° C. and a freezing point of 16.8° C., and the use amount of sulfuric anhydride is extremely small, therefore, handling thereof is very difficult. Then, conventionally, sulfuric anhydride is dissolved in acetone to prepare a sulfuric anhydride acetone solution having a concentration of 0.01 to 10.0 wt %, and the solution is fed as a catalyst to a reactor for acidolysis (e.g. JP 9-143111A).

Though there are no detailed descriptions on a preparation method of the sulfuric anhydride acetone solution, a method of dropping or feeding sulfuric anhydride which is liquid at normal temperature into acetone solvent, is simple, therefore, this method has been usually used. However, in the catalyst prepared by this method, scale produces. Therefore, there were problems on stable operation of the production plant because it was necessary to remove frequently the scale produced in a preparation vessel, and to clean frequently a strainer of a catalyst feeding pump used for supplying the sulfuric anhydride acetone solution as a catalyst to a reactor for acidolysis of di(2-hydroperoxy-2-propyl)benzene, and a feed line to the reactor was clogged with scale.

SUMMARY OF THE INVENTION

As a result of studies regarding the cause of scale production, the present inventors found that a contact portion of liquid sulfuric anhydride and a ketone solvent is locally heated in preparing a catalyst, and condensation products and the like are caused by thermal reactions, supposedly decomposition and condensation, of the ketone solvent. Further, the present inventors have intensively studied to solve the above-mentioned problems, and resultantly found that a catalyst producing little scale can be prepared, leading to completion of the present invention.

An object of the present invention is to provide a catalyst for acidolysis of an aromatic hydroperoxy compound, containing a small amount of sulfuric anhydride and little scale in a ketone solvent, and a process for producing an aromatic hydroxy compound, which can be stably operated, using the catalyst.

Namely, the present invention provides a catalyst for acidolysis of an aromatic hydroperoxy compound, prepared by a process comprising gasifying liquid sulfuric anhydride and dissolving gasified sulfuric anhydride in a ketone solvent.

Further, the present invention provides a process for producing an aromatic hydroxy compound, which comprises subjecting an aromatic hydroperoxy compound to acidolysis in the presence of the above-mentioned catalyst.

DETAILED DESCRIPTION OF THE INVENTION

As the ketone solvent used for dissolving a gasified sulfuric anhydride, acetone, methyl ethyl ketone and methyl isobutyl ketone and the like are listed, and acetone and methyl isobutyl ketone are preferable, and acetone is most preferable. The ketone solvents may be used singly or in admixture of two or more.

The method of gasifying liquid sulfuric anhydride for preparation is conducted, for example, as described below.

A flow rate of liquid sulfuric anhydride is controlled by a flow meter and control valve so as to provide a dilute solution having a concentration of sulfuric anhydride of about 0.01 to about 10 wt %, then, liquid sulfuric anhydride is transported to a heater (including, a heat exchanger) by a pump or the like, and it is heated there to gasify liquid sulfuric anhydride. The heating temperature may advantageously be a temperature at which liquid sulfuric anhydride is gasified, and it is suitable to conducted heating to temperatures of the boiling point or lower of the ketone solvent. When dissolved in acetone, it is usually suitable to conducted heating up to about 55° C. The gasified sulfuric anhydride is mixed with the ketone solvent. The mixing method is not particularly restricted. For example, when gaseous sulfuric anhydride is fed to a preparation vessel containing a ketone solvent for mixing and the gas is bubbled through the ketone solvent for mixing, the position of a feed nozzle for the sulfuric anhydride gas is set or the liquid surface of the solvent is controlled so that the nozzle position is in the liquid of the solvent. In mixing, a stirrer may be used for further improving contact with a solvent. Regarding feeding of sulfuric anhydride to a heater and preparation vessel, sulfuric anhydride in a predetermined amount may be continuously transported using a pump and flow meter as described above, alternatively, after measurement of a predetermined amount of sulfuric anhydride using a meter, it may also be sequentially fed to a heater and preparation vessel by a pump or a pressure of an inert gas such as nitrogen.

The ketone solution of sulfuric anhydride as an acidolysis catalyst thus prepared contains little scale.

Using a dilute solution of sulfuric anhydride prepared as described above as a catalyst, an aromatic hydroperoxy compound can be subjected to acidolysis to obtain an aromatic hydroxy compound.

The aromatic hydroperoxy compound is usually a compound to be converted into an aromatic hydroxy compound by acidolysis, and examples thereof include monoalkyl hydroperoxybenzenes such as 2-hydroperoxy-2-propylbenzene (cumene hydroperoxide), and di(alkylhydroperoxy)benzenes such as di(2-hydroperoxy-2-propyl)benzenes (including 1,3-, 1,4- and 1,2-di(2-hydroperoxy-2-propyl)benzene), and by subjecting these compounds to acidolysis, hydroxy benzenes such as phenol or 1,3-, 1,4- and 1,2-dihydroxybenzenes can be obtained.

Particularly, the catalyst of the present invention is used in a reaction for the acidolysis of preferably di(alkyl hydroperoxy)benzenes, more preferably of 1,3-, 1,4- and 1,2-di(2-hydroperoxy-2-propyl)benzene.

The aromatic hydroperoxy compound can be obtained by known oxidation reactions of alkylbenzenes (e.g. cumene, 1,3-, 1,4- and 1,2-diisopropylbenzene).

Further, the acidolysis is conducted by feeding the catalyst to a reactor to acidolyze an aromatic hydroperoxy compound, in other words, by contacting the aromatic hydroperoxy compound with the catalyst for acidolysis, and an aromatic hydroxy compound is thus obtained.

Acidolysis conditions are not particularly restricted and known conditions are adopted. Preferably, the reaction temperature is from 60 to 100° C., pressure is from 200 to 700 Torr and time is from 1 to 15 minutes.

EXAMPLE

The present invention will be described in detail by the following Examples.

Example 1

After a flow rate of liquid sulfuric anhydride was controlled by a flow meter and control valve so as to provide a 0.8 wt % sulfuric anhydride acetone solution, then, the liquid sulfuric anhydride was transported to a heater by a pump, and heated there up to about 55° C., to gasify the liquid sulfuric anhydride. The gasified sulfuric anhydride was transported to a preparation vessel filled with acetone of about 15° C., the liquid surface was controlled so that the position of a feed nozzle for a sulfuric anhydride gas was in the solvent, and gaseous sulfuric anhydride was bubbled to dissolve it in acetone. Little formation of scale in the preparation vessel was observed. The acetone solution of sulfuric anhydride thus prepared was continuously fed as a catalyst for acidolysis to a reactor with a feed pump, to carry out acidolysis of 1,3-di(2-hydroperoxy-2-propyl)benzene. A strainer of the feed pump of the liquid catalyst showed no clogging during acidolysis, and a stable operation for a period of longer than 1 month was possible.

Comparative Example 1

A flow rate of liquid sulfuric anhydride was controlled by a flow meter and control valve so as to provide a 0.8 wt % sulfuric anhydride solution, the liquid sulfuric anhydride was transported to a preparation vessel filled with acetone of about 15° C. with a feed pump, and mixed with acetone. The liquid surface was controlled so that the position of a feed nozzle for a sulfuric anhydride gas was in the solvent, and the liquid sulfuric anhydride was dissolved in acetone while stirring. Formation of scale in the preparation vessel was observed, and removal of scale in the preparation vessel once every one week was necessary. The acetone solution of sulfuric anhydride thus prepared was fed to a reactor in which 1,3-di(2-hydroperoxy-2-propyl)benzene was charged, to effect acidolysis of 1,3-di(2-hydroperoxy-2-propyl)benzene. As a result, a strainer of a catalyst liquid feed pump showed clogging, and it was necessary to conduct cleaning of the strainer once every one week.

As described above, by gasifying sulfuric anhydride and dissolving it in a ketone solvent, it becomes possible to prepare a catalyst for acidolysis of sulfuric anhydride, showing no generation of scale in preparing a dilute solution of sulfuric anhydride, and by conducting acidolysis of an aromatic hydroperoxy compound, a process for producing a hydroxy aromatic compound which can be operated stably, can be provided.

What is claimed is:

1. A catalyst for the acidolysis of an aromatic hydroperoxy compound, prepared by a method comprising gasifying liquid sulfuric anhydride and dissolving gasified sulfuric anhydride into a ketone solvent.

2. The catalyst according to claim 1, wherein the ketone solvent is acetone and/or methyl isobutyl ketone.

3. The catalyst according to claim 2, wherein the ketone solvent is acetone.

4. A process for producing an aromatic hydroxy compound, which comprises subjecting an aromatic hydroperoxy compound to an acidolysis in the presence of the catalyst of claim 1.

5. A process for producing an aromatic hydroxy compound, which comprises subjecting an aromatic hydroperoxy compound to an acidolysis in the presence of the catalyst of claim 2.

6. A process for producing an aromatic hydroxy compound, which comprises subjecting an aromatic hydroperoxy compound to an acidolysis in the presence of the catalyst of claim 3.

7. The process according to claim 4, wherein, the aromatic hydroperoxy compound is a di(hydroperoxyalkyl)benzene.

8. The process according to claim 5, wherein, the aromatic hydroperoxy compound is a di(hydroperoxyalkyl)benzene.

9. The process according to claim 6, wherein, the aromatic hydroperoxy compound is a di(hydroperoxyalkyl)benzene.

10. The process according to claim 7, wherein, the di(hydroperoxyalkyl)benzene is di(2-hydroperoxy-2-propyl)benzene.

11. The process according to claim 8, wherein, the di(hydroperoxyalkyl)benzene is di(2-hydroperoxy-2-propyl)benzene.

12. The process according to claim 9, wherein, the di(hydroperoxyalkyl)benzene is di(2-hydroperoxy-2-propyl)benzene.

* * * * *